United States Patent [19]
Rodak

[11] Patent Number: 5,470,009
[45] Date of Patent: Nov. 28, 1995

[54] SURGICAL FASTENING APPARATUS WITH LOCKING MECHANISM

[75] Inventor: Daniel Rodak, Milford, Conn.

[73] Assignee: United States Surgical Corporation, Norwalk, Conn.

[21] Appl. No.: 270,396

[22] Filed: Jul. 5, 1994

Related U.S. Application Data

[63] Continuation of Ser. No. 936,884, Aug. 27, 1992, abandoned, which is a continuation of Ser. No. 622,856, Dec. 6, 1990, abandoned.

[51] Int. Cl.$^6$ ................................................. A61B 17/072
[52] U.S. Cl. ........................... 227/176; 227/8; 227/19; 227/178
[58] Field of Search .......................... 227/8, 19, 175, 227/176, 177, 178, 179, 180, 181, 182

[56] References Cited

U.S. PATENT DOCUMENTS

| | | |
|---|---|---|
| D. 283,733 | 5/1986 | Rawson et al. ............. D24/26 |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. . |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein ................. 227/19 X |
| 4,006,786 | 2/1977 | Speicher . |
| 4,086,926 | 5/1978 | Green et al. . |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky ............. 227/19 X |

(List continued on next page.)

FOREIGN PATENT DOCUMENTS

| | | |
|---|---|---|
| 5476486 | 9/1986 | Australia . |
| 5476586 | 9/1986 | Australia . |
| 0324638 | 7/1989 | European Pat. Off. . |
| 0373762 | 6/1990 | European Pat. Off. . |
| 0380025 | 8/1990 | European Pat. Off. . |
| 0489436 | 6/1992 | European Pat. Off. . |
| 2070499 | 9/1981 | United Kingdom . |
| 8302247 | 7/1983 | WIPO . |

OTHER PUBLICATIONS

"Disposable EEA Surgical Stapler and Curved Disposable EEA Surgical Stapler", Information Booklet, printed Jan. 1985.

Anderson et al., Surgical Stapling, "Thoraci, Vascular and Esophageal Procedures", pp. 1–101, 1988.

Brolin et al., Surgical Stapling, "Bariatric Procedures for Morbid Obesity", pp. 1–115, 1989.

Flickinger et al., Surgical Stapling, "Gastric and Small Bowel Procedures", pp. 1–145, 1988.

"Auto Suture® Premium Poly CS™–57 Disposable Surgical Stapler," printed 1986, reprinted 1990.

"Auto Suture® Poly CS™–57 Disposable Surgical Stapler", printed Jul. 1988.

"Auto Suture® Poly CS™–57 Disposable Loading Units with LACTOMER® Absorbable Copolymer Staples", printed Jul. 1988.

*Primary Examiner*—Rinaldi I. Rada

[57] ABSTRACT

An improved apparatus for applying surgical fasteners to body tissue comprising a cartridge containing a plurality of fasteners, an anvil positioned opposite the cartridge, and a locking mechanism to prevent re-approximation of the cartridge towards the anvil when the cartridge is withdrawn from the anvil after the fasteners are fired. The locking mechanism comprises a leaf spring clip with a distal hook for engaging a slot on the anvil support arm. The clip is moved distally when the staples are fired, and the hook engages the slot when the fastener holding cartridge is moved to the open position to release the body tissue.

54 Claims, 6 Drawing Sheets

U.S. PATENT DOCUMENTS

| | | |
|---|---|---|
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque .................... 227/8 |
| 4,349,028 | 9/1982 | Green .................... 227/19 |
| 4,354,628 | 10/1982 | Green .................... 227/19 |
| 4,383,634 | 5/1983 | Green . |
| 4,391,401 | 7/1983 | Moshofsky . |
| 4,415,112 | 11/1983 | Green . |
| 4,429,695 | 2/1984 | Green . |
| 4,442,964 | 4/1984 | Becht . |
| 4,473,077 | 9/1984 | Noiles et al. . |
| 4,480,640 | 11/1984 | Becht .................... 72/410 |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. .................... 227/8 |
| 4,527,724 | 7/1985 | Chow et al. .................... 227/8 |
| 4,530,453 | 7/1985 | Green . |
| 4,540,110 | 9/1985 | Bent .................... 227/8 |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | DiGiovanni .................... 227/8 |
| 4,592,498 | 6/1986 | Braun et al. .................... 227/19 X |
| 4,597,517 | 7/1986 | Wagdy .................... 227/8 |
| 4,605,004 | 8/1986 | Di Giovanni et al. . |
| 4,606,344 | 8/1986 | Di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green .................... 227/19 X |
| 4,684,051 | 8/1987 | Akopov et al. . |
| 4,714,187 | 12/1987 | Green . |
| 4,715,520 | 12/1987 | Roehr, Jr. et al. . |
| 4,728,020 | 3/1988 | Green et al. . |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. . |
| 4,869,415 | 9/1989 | Fox . |
| 4,881,544 | 11/1989 | Green et al. . |
| 4,881,545 | 11/1989 | Isaacs et al. . |
| 4,892,244 | 1/1990 | Fox et al. .................... 227/8 |
| 4,915,100 | 4/1990 | Green . |
| 4,938,408 | 7/1990 | Bedi et al. .................... 227/8 |
| 4,941,623 | 7/1990 | Pruitt . |
| 4,955,959 | 9/1990 | Tompkins .................... 227/180 X |
| 5,031,814 | 7/1991 | Tompkins et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins . |
| 5,129,570 | 7/1992 | Schulze et al. . |

SURGICAL FASTENING APPARATUS WITH LOCKING MECHANISM

This is a continuation of U.S. application Ser. No. 07/936,884 filed on Aug. 27, 1992, which is a continuation of U.S. application Ser. No. 07/622,856 filed on Dec. 6, 1990 both abandoned.

BACKGROUND OF THE INVENTION

1. Field of the Invention

This invention relates to surgical fastening apparatus, and specifically to an improved surgical fastening apparatus containing a locking mechanism.

2. Background of the Art

Surgical fastening apparatus for simultaneously applying an array of surgical staples or other types of fasteners are known in the art. Such apparatus are used for suturing body tissue such as, for example, intestinal and gastric walls with spaced parallel rows of longitudinally aligned staples. These surgical stapling apparatus reduce the time of wound closure in a surgical procedure.

Typically these apparatus include a fastener holder disposed on one side of the tissue to be fastened, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. Optionally, the fastening apparatus may include a knife mechanism for creating an incision between rows of fasteners. The fasteners can be made of metal, non-absorbable polymers, or bioabsorbable polymers such as polyglycolide, polylactide, and copolymers thereof.

In common use are apparatus in which the fastener holder comprises a disposable cartridge removably mounted in or on a permanent actuator for supporting and actuating the cartridge. The cartridge is disposable after a single use, i.e. after the fasteners are fired. The permanent actuator is reusable in the same surgical procedure after reloading with a fresh cartridge, and is reusable in another surgical procedure after cleaning, sterilizing, and reloading. Also known are disposable surgical apparatus, in which the entire apparatus is disposed of after use. Examples of surgical stapling apparatus may be found in Green (U.S. Pat. No. 4,354,628), Green (U.S. Pat. No. 4,665,916), and Rawson et al. (U.S. Pat. Des. No. 283,733).

In the use of surgical fasteners the possibility arises that the fastener apparatus may be actuated when the cartridge is empty of staples (fasteners). This can occur when the apparatus has been fired once, but the cartridge is not reloaded or discarded. This can also occur if the apparatus is inadvertently reloaded with a spent cartridge. Under such circumstances the fastening apparatus will fail to suture the body tissue, which can cause harm to the patient and result in the surgeon's loss of valuable time. The risk of harm is greatly increased if the apparatus contains a knife mechanism, since it will create an unsealed incision. To eliminate these dangers to the patient it would be beneficial to provide a mechanism which alerts the user that a new cartridge is required. It would further be beneficial if such a mechanism can provide a lock to actually prevent the surgeon from trying to fire a cartridge that has already been fired and prevent reloading of a spent cartridge. This would save valuable time and reduce the risks to the patient.

SUMMARY OF THE INVENTION

The present invention provides a surgical fastening apparatus which achieves the aforementioned benefits. An apparatus is provided for applying to body tissue a plurality of surgical fasteners. The apparatus has a cartridge containing a plurality of fasteners, an anvil positioned opposite the cartridge for closing (crimping) the fasteners, means for approximating the cartridge toward the anvil to grip body tissue therebetween when the apparatus is closed, and means for preventing (blocking) re-approximation of the cartridge after the cartridge is spent (i.e. the fasteners have been fired) and the cartridge is withdrawn from the anvil. Preferably, the cartridge is removable such that it can be removed after the fasteners are fired, and replaced with another loaded removable cartridge.

The apparatus includes a locking mechanism associated with the cartridge which is engageable with interference means in the apparatus to prevent the apparatus from reclosing with the spent cartridge.

The lockout mechanism is preferably at least partially located inside of the cartridge. Actuation of the lockout mechanism includes movement of the lockout mechanism from an initial position within the cartridge to a position wherein at least a portion of the lockout mechanism extends beyond the periphery of the cartridge so as to become engageable with the approximation blocking means.

BRIEF DESCRIPTION OF THE DRAWINGS

The invention is described in more detail hereinbelow wherein.

DETAILED DESCRIPTION OF THE INVENTION

Figure 1:
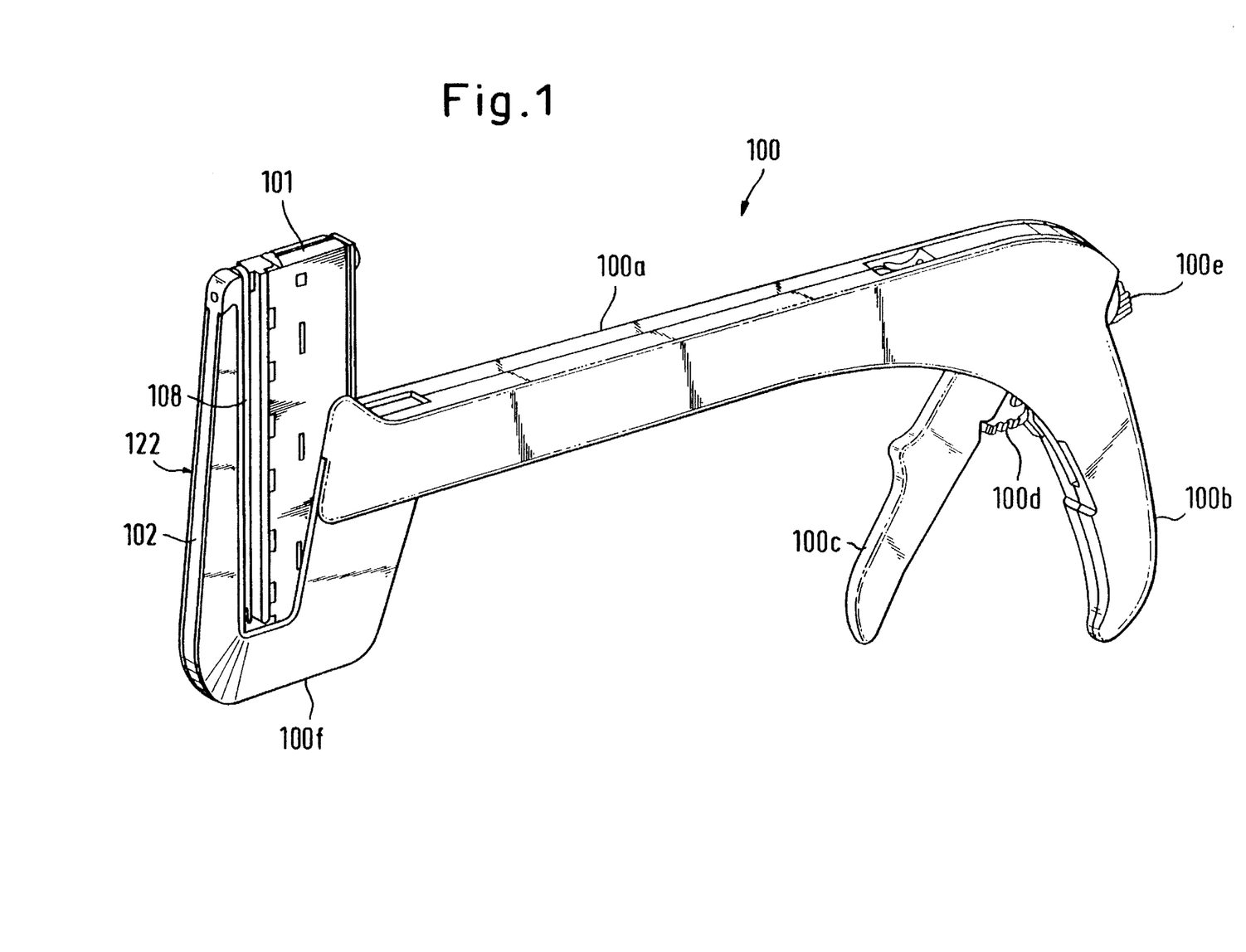
FIG. 1 illustrates a fastener applying apparatus in elevated perspective view.

FIG. 1 illustrates a surgical stapler 100 having an elongated carrier portion 100a, a handle 100b, an actuating lever or trigger 100c, a safety latch 100d for locking the trigger 100c, an approximating lever 100e, a U-shaped distal portion 100f, a staple holder cartridge 101, and an anvil assembly 122 comprising an anvil 108 for closing or crimping the staples and an anvil support arm 102. The instrument operates by positioning body tissue between the staple holder cartridge 101 and the anvil 108, then, by pivoting the approximating lever 100e, pivoting and sliding the staple cartridge 101 into a closed position wherein it is in close approximation to the anvil 108 so that it can grip tissue held therebetween. Next, the apparatus is fired by pressing the trigger 100c towards handle 100b, thereby driving surgical staples into the body tissue, the staple legs being crimped by anvil 108. Finally, the apparatus is opened by pivoting the approximation lever 100e to withdraw the cartridge 101 proximally away from the anvil assembly, thereby releasing the body tissue.

The term "fasteners" is used herein as a generic term which includes surgical staples, and the staple-shaped portion of two-part surgical fasteners, and equivalents thereof. Thus, although the surgical fastener of the present invention is exemplified in FIGS. 1–3 as a staple embodiment, the inventive features described herein are applicable to instruments for applying metal staples, as well as staples and two-part fasteners made from non-bioabsorbable or from bioabsorbable polymers (e.g. polyglycolide, polylactide and copolymers thereof). A two-part fastener is illustrated in FIG. 4. Unlike one piece staples which are closed by crimping the legs, the two piece fasteners are typically closed by joining and interlocking the two parts of the fasteners together. Typically, a two-part fastener includes a fastener portion 151 and a retainer portion 152. The fastener portion has prongs 153 which are adapted to be received into apertures 154 in the retainer and locked therein. The term "anvil assembly" is used herein as a generic term to include the anvil used to clinch surgical staples, the retainer holder and retainer member of two-part resinous surgical fasteners, and the equivalent of these elements. The anvil assembly of a fastener applying instrument holds the retainer portions until the fasteners are locked therein, whereupon the retainers are released.

Thus, the present invention should not be construed as being limited only to instruments for applying metal staples, but rather more generally to surgical fastener applying apparatus.

The locking mechanism of the present invention enables the apparatus to be fired only once in a single use, as it prevents re-approximation of cartridge 101 after the fasteners have been fired and the cartridge 101 is retracted to its open position. If the cartridge 101 is adapted to be disposable and replaceable the apparatus can be retired by substituting a new cartridge loaded with staples. If reloaded with a spent (already fired) cartridge, the locking mechanism will prevent approximation of the cartridge and thereby not allow the instrument to be fired.

In general, the apparatus of the present invention includes a locking mechanism mounted for interaction with the cartridge and an interference means, i.e. an approximation blocking means, associated with the anvil assembly. The approximation blocking means cooperates with the locking mechanism to prevent closure of the apparatus, that is, the cartridge 101 cannot be moved into close approximation with the anvil 108. In the illustrated embodiment (FIG. 2A), the approximation blocking means comprises a slot 104 formed in the anvil support arm 102 to provide a blocking surface at approximately a right angle to the motion of the cartridge. Alternately, one or more slots at differing angles could be provided to receive the locking mechanism. Clearly, the number, position, and configuration of the slots will vary depending on the locking mechanism employed. For example, if the locking mechanism is designed to extend linearly, the slot will extend longitudinally. Moreover, other blocking means besides slots can be provided as long as they achieve the function of engaging the locking mechanism to restrict movement of the cartridge.

As noted above, the locking mechanism of the present invention serves as a safety member which interacts with the cartridge and cooperatively engages the approximation blocking means so as to prevent distal movement of the cartridge beyond a predetermined position. The lockout mechanism is actuated after two movements have been completed: 1) firing of the fasteners from the cartridge, and 2) reopening the apparatus i.e. proximal movement of the cartridge to permit removal of tissue.

Figure 2A:
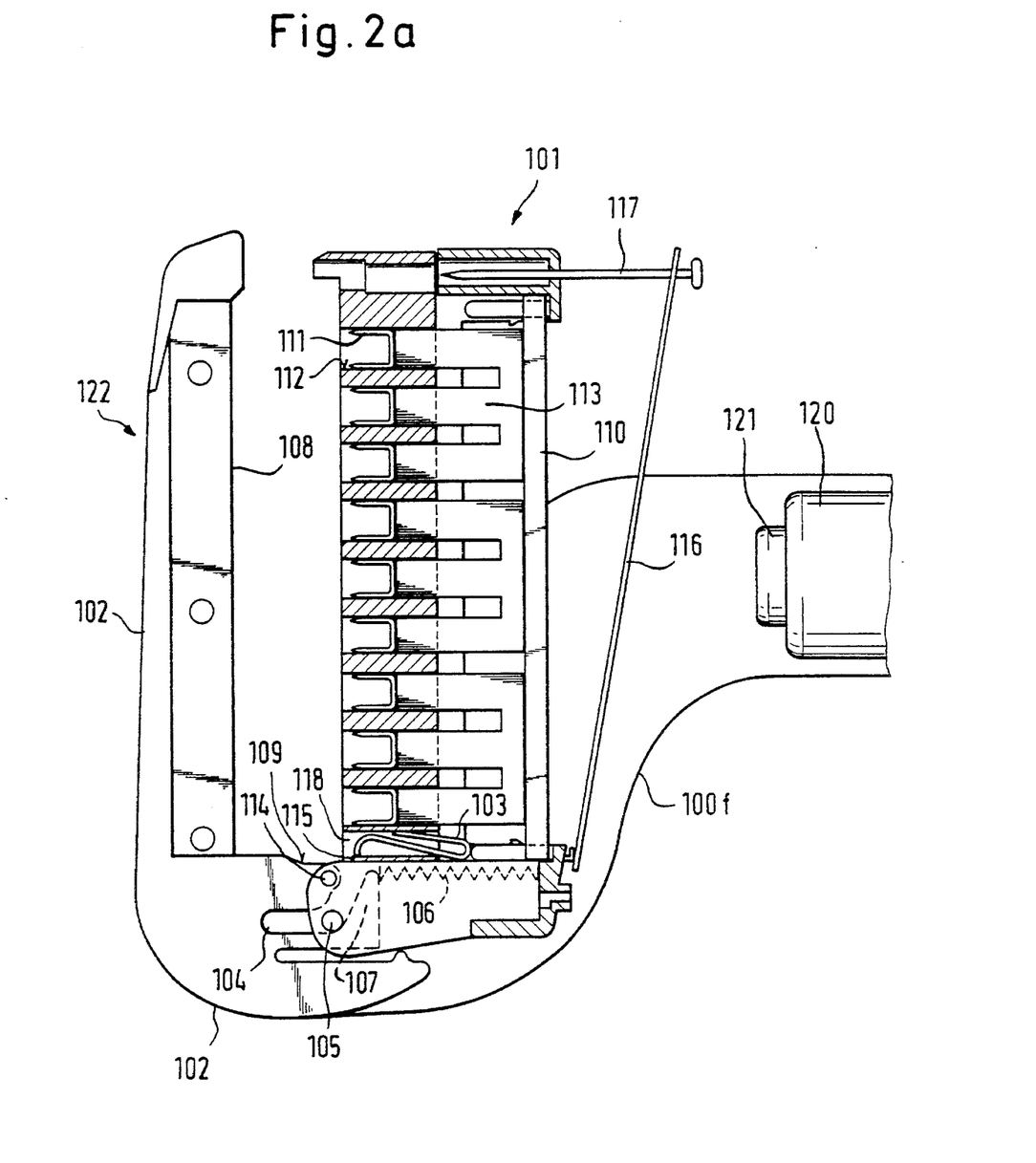
FIGS. 2a, 2b and 2c, illustrate in elevational sectional view the distal portion of the fastener applying apparatus in the pre-firing, fired, and after firing positions, respectively.
Figure 2B:
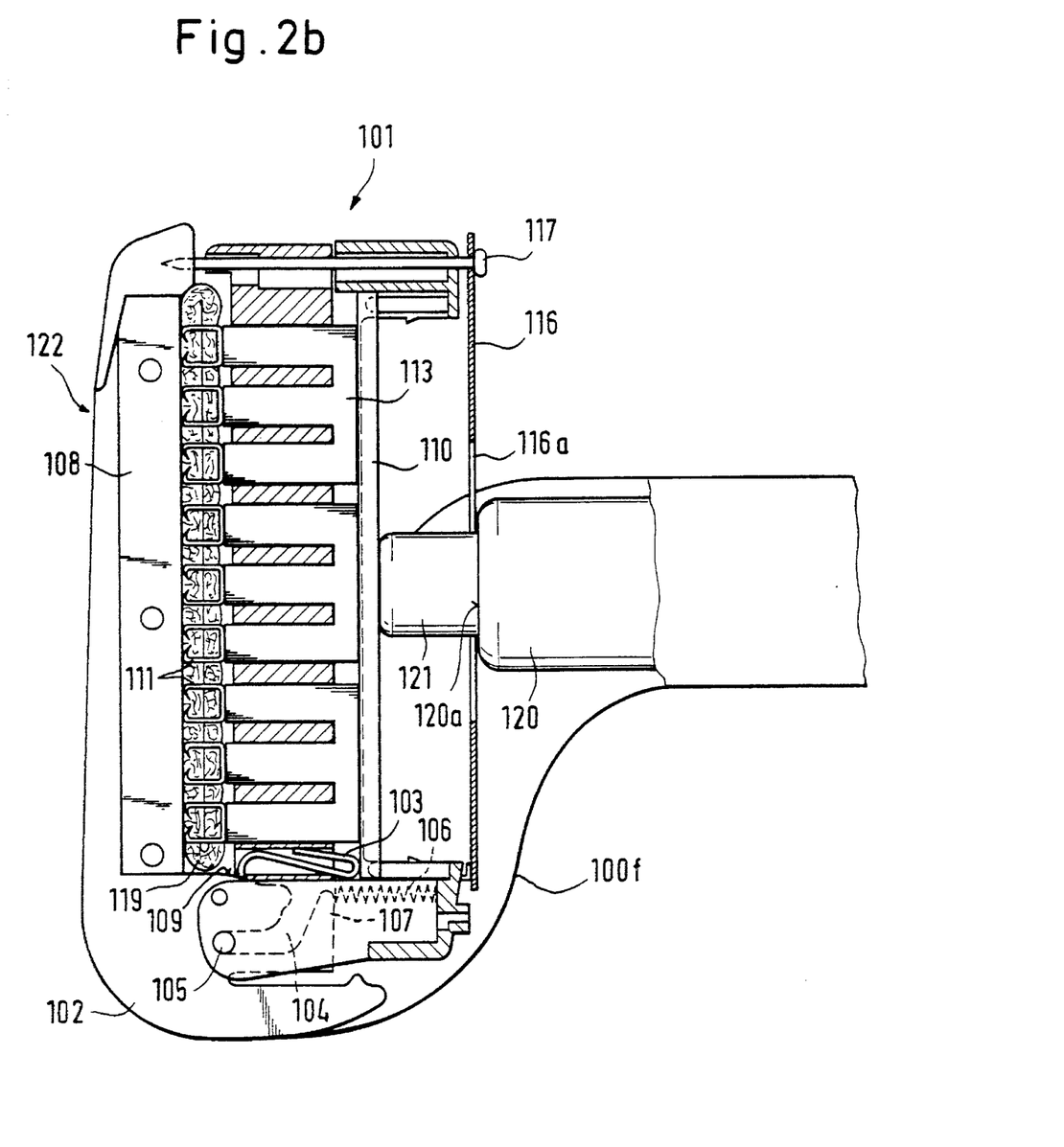
Figure 2C:
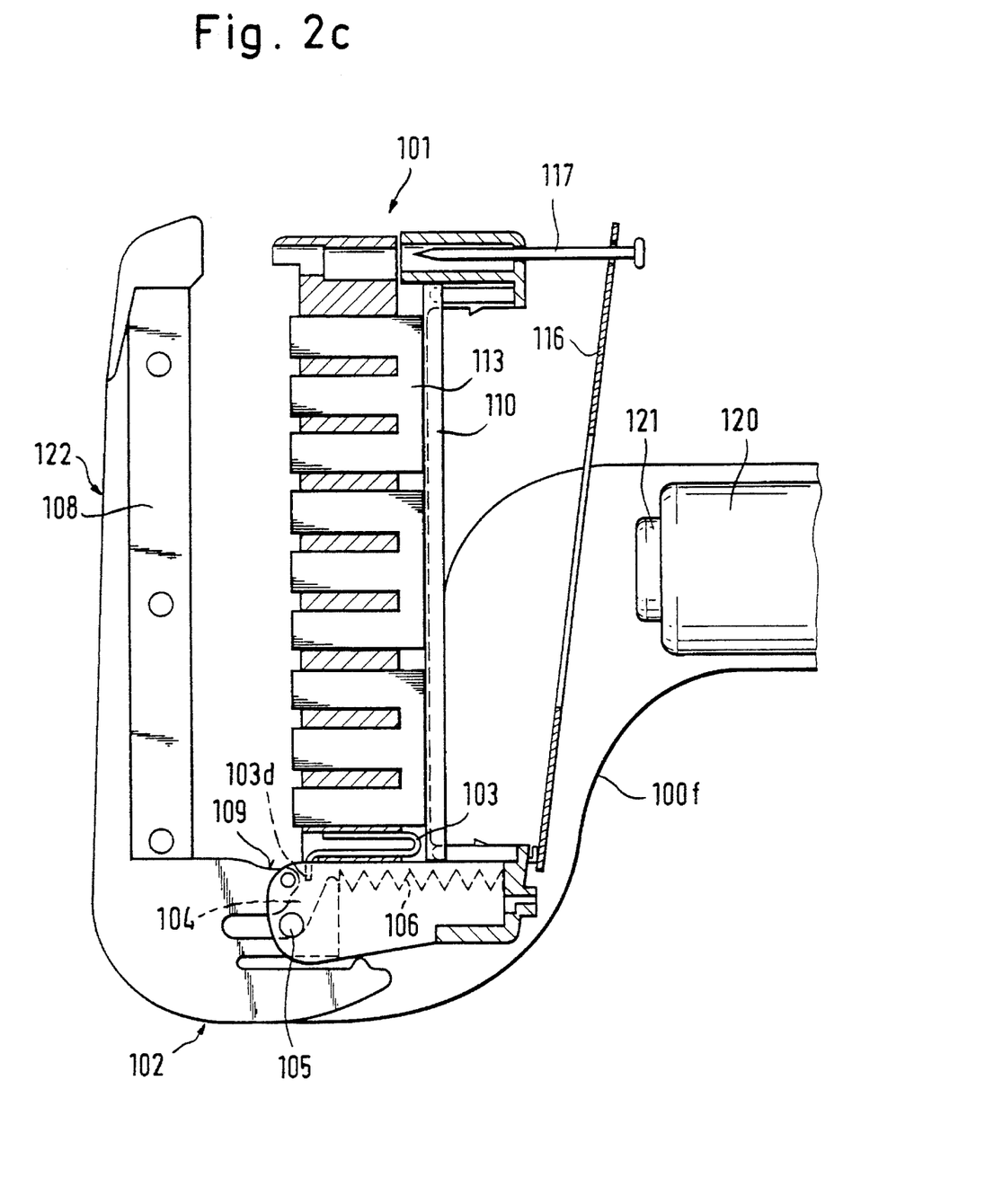
Figure 3A:
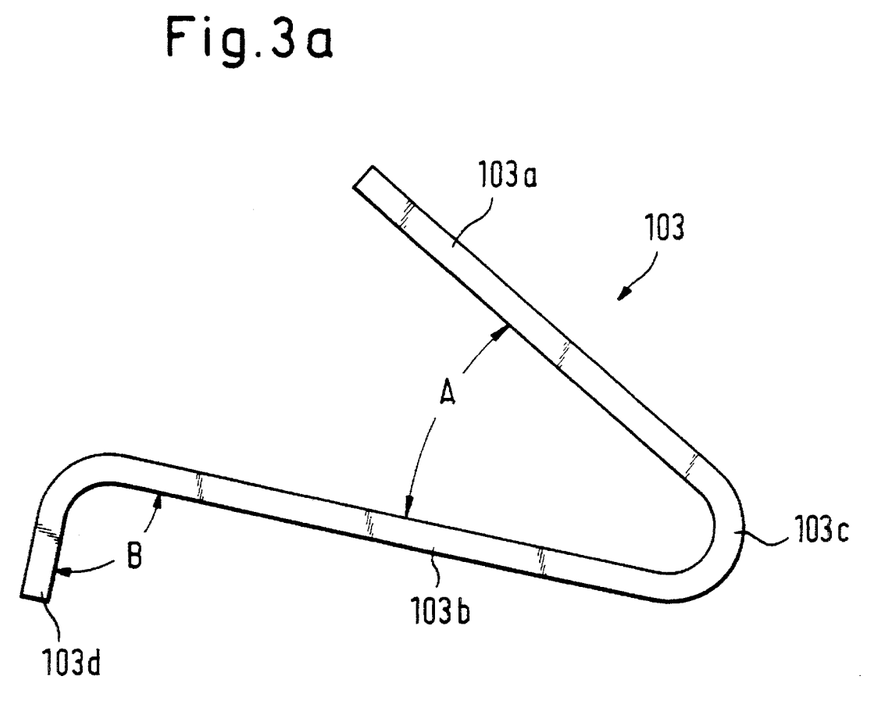
FIG. 3a illustrates a side view of the resilient locking clip.
Figure 3B:
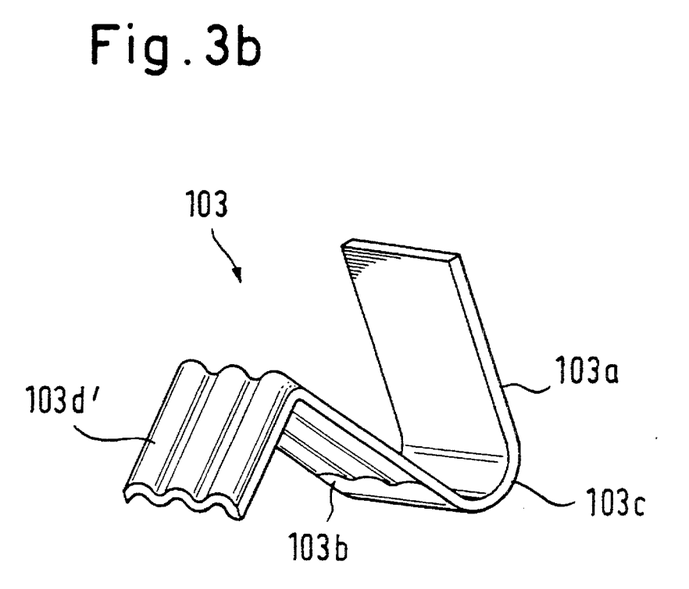
FIG. 3b is a perspective view of an alternative locking clip with ribbed hook portion.
Figure 4:
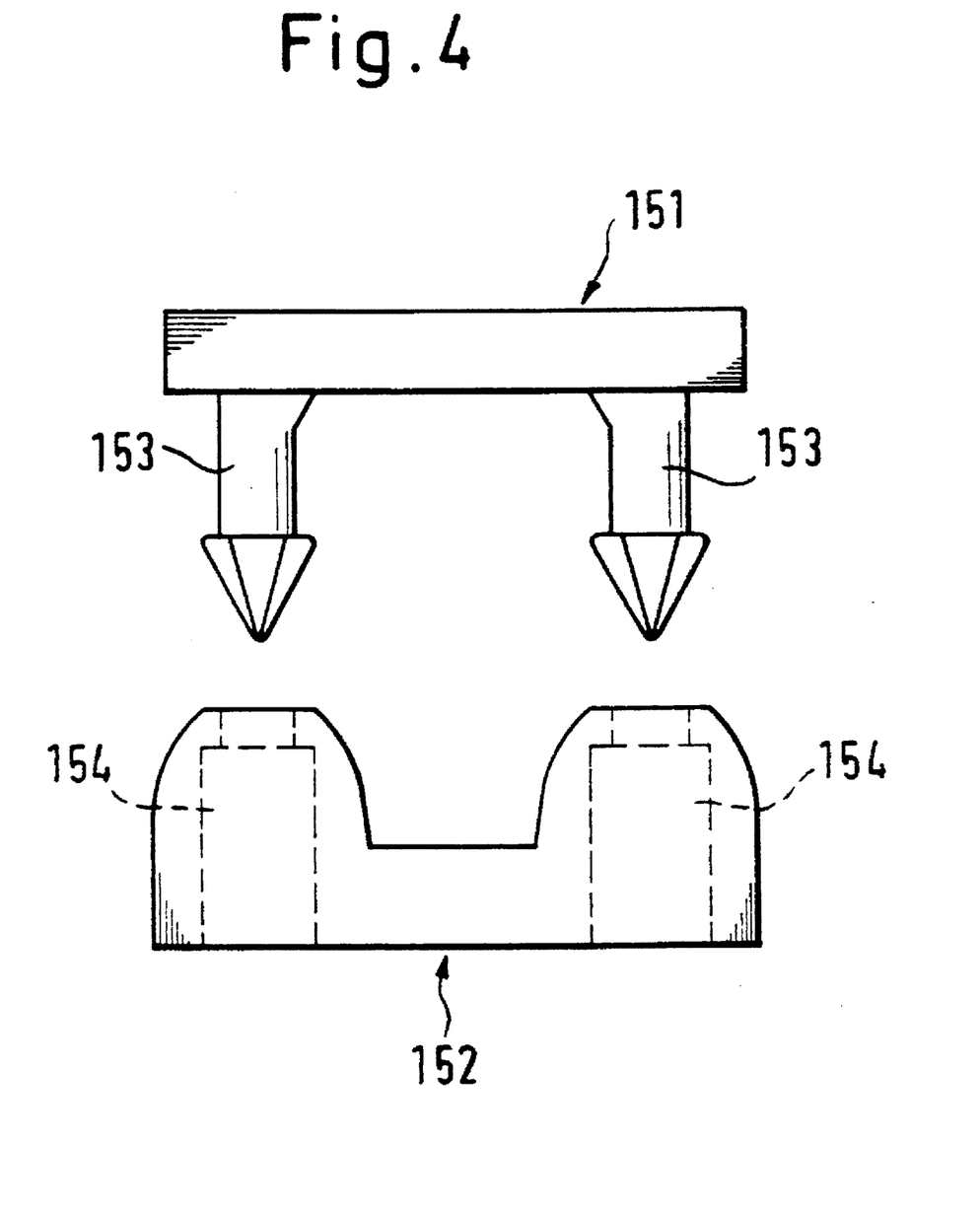
FIG. 4 is a side elevational view of a two-part surgical fastener.

In the embodiment shown in FIGS. 2 and 3, approximation blocking means is in the form of slot 104. The locking mechanism in this embodiment is designated by reference numeral 103 and includes a detent or hook 103d for engaging the slot. Cooperation between the locking mechanism and the walls of the slot 104 prevents movement of the cartridge 101 from the open (proximal) to the closed (distal) position. The hook 103d is moved out of its pre-fired position and into engagement with the slot 104 in response to actuation of the fastener driver which fires the fastener. The locking mechanism 103 is associated with the cartridge 101 so that removal and replacement of the cartridge effects a change of lockout mechanisms as well.

More specifically, the single use locking mechanism 103 in the embodiment of FIGS. 2 and 3 comprises locking clip 103 which is slidably mounted within chamber 118 of the cartridge 101. Referring additionally now to FIGS. 3a and 3b, locking clip 103 is preferably in the form of a leaf spring having a first, upper arm portion 103a and a second, lower arm portion 103b which are integrally united at curved proximal end 103c, and a hook or detent 103d projecting downwardly from the distal end of the lower arm 103b. The upper arm 103a and lower arm 103b define an angle "A" which is about 10° to 50° depending on material thickness and condition, and preferably about 30°. The lower arm 103b and the hook 103d define an angle "B" which is preferably from about 75° to 120°. This area may be ribbed to provide additional resistance to bending when actuated. FIG. 3b illustrates a locking clip 103 with ribbed hook 103d'. The ribs may optionally also extend along lower arm 103b. The upper arm 103a is braced against the roof of the chamber 118, thereby providing a biasing force to resiliently urge lower arm 103b in a downward direction retaining the locking clip 103 in a free-movement position. The lower arm 103b illustratively extends longitudinally beyond that of upper arm 103a so that when the locking clip is moved distally as discussed below, the distal end of lower arm 103b with hook 103d is pushed outside chamber 118 while the upper arm 103a is still maintained inside the chamber 118 for providing the downward biasing force. In the initial position of locking clip 103, the hook 103d rests on base 115, which is preferably a strip of metal defining the floor of chamber 118. In this position the detent 103d is non-engageable with slot 104 and affords movement of the cartridge.

The hook can be integrally connected into a single piece to the locking clip in, for example, a resilient clip or a leaf spring with a hooked end. Alternately, the hook can be a separate piece connected to the locking clip.

FIG. 2a illustrates the distal portion of the apparatus 100 including the locking mechanism. In this embodiment the hook and locking member are integral. Fastener holder 101 is typically a rectangular shaped replaceable cartridge which is pivotally and slidably mounted to the anvil support arm 102 via mounting pin 105. The mounting pin 105, which is fixed to the lower portion of the staple cartridge 101, is adapted to be received into mounting slot 104 of the anvil support arm 102. Staples 111 are disposed within slotted grooves 112, and are pushed distally towards the anvil assembly by staple drivers 113 when the instrument is fired. The anvil assembly 122 comprises the anvil support arm 102 and, seated in the anvil support arm 102, an anvil 108 for crimping the legs of staples 111. Alignment pin 117, which is mounted to leaf spring 116, serves to align the cartridge 101 when the cartridge 101 is closed onto the body tissue.

Spring 106 biases the cartridge 101 proximally, i.e., away from anvil assembly 122. The distal end of spring 106 abuts the proximal end of post 107, which is an integral part of anvil support arm 102.

Projections 114 project outwardly from the cartridge 101, and are adapted to abut the edge of U-shaped distal portion 100f when the apparatus is closed. Projections 114 serve to align the cartridge 101.

Further illustrations of fastener cartridges may be found in U.S. Pat. Nos. 4,568,009 and 4,915,100, herein incorporated by reference.

FIG. 2b illustrates the cartridge 101 in the fired position. Actuator 120 is moved distally when release toggle 100e is rotated clockwise, and the camming surface 120a is biased into contact with leaf spring 116. This moves the cartridge distally to close the apparatus on body tissue 119 located between the cartridge 101 and the anvil 108. Upon moving distally, spring 106 is compressed which then exerts a force for proximally biasing the cartridge back into the open position when the release toggle 100e is opened. When the actuating lever 100c is rotated counterclockwise, driver 121 is moved distally into contact with the pusher bar 110, moving the pusher bar 110 distally. The pusher bar, in turn, moves staple drivers 113 distally, thereby driving staples 111 through body tissue 119 and into the anvil 108 where the staple legs are crimped.

Upon moving distally, the pusher bar 110 also pushes locking clip 103 distally such that the hook 103d is moved out of chamber 118 and onto the sloped contact surface 109 of the anvil support arm 102. In this intermediate position, the hook does not yet engage the approximation blocking means.

After the stapling is completed, the apparatus is opened by rotating the approximating lever 100e counterclockwise back into the open position. As can be seen in FIG. 2c, after firing and release of approximation lever 100e, the cartridge 101 is moved proximally back into the open position to release the body tissue which was operated upon. However, the locking clip 103 does not fully return into chamber 118. Rather, the hook 103d slides down surface 109 and into the mouth of slot 104. The hook is held in this position by spring tension to prevent dislodging. Slot 104 in the anvil assembly thereby provides a catch means for engaging hook 103d. Once engaged therein, the locking clip prevents the apparatus from being reclosed, for if the user once again attempts to rotate lever 100e, the distal hook 103d will abut the edge of sloping surface 109 thereby preventing the cartridge 101 from being moved distally by actuator 120. At this time, either the expended cartridge can be removed, discarded, and replaced with a new cartridge, or the entire instrument can be discarded for a new instrument. The locking clip also prevents a fired or spent cartridge which has been removed and reinserted, from being closed since a spent cartridge when loaded will have its hook 103d seated in slot 104. An unfired cartridge on the other hand will have its hook 103d resting on the base 115 of the chamber 118 and therefore out of engagement with the slot in the anvil arm when inserted into the apparatus.

Clearly, other locking mechanisms could be provided which prevent approximation of the cartridge. In an alternate embodiment, the locking mechanism can be a T-shaped member pivotally mounted within the cartridge and removably held in sideways (longitudinal) position such that the trunk portion of the T is distally oriented. After firing of the fasteners, the T-shaped member is released. When the apparatus is opened, the T-shaped lockout member pivots downward and into alignment with a slot in the anvil assembly. If the user attempts to reclose the apparatus, the trunk portion of the T-shaped locking mechanism will abut the wall of the aperture and prevent further distal movement of the cartridge.

In another embodiment, the locking mechanism may comprise a slidable shaft which is released upon firing of the apparatus, and which slides downwardly into a slot when the apparatus is opened (i.e. the cartridge is moved proximally) so that a portion of it protrudes beyond the lower surface of the cartridge thereby interfering with distal movement of the cartridge if an attempt is made to reclose the apparatus.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An apparatus for applying a plurality of surgical fasteners to body tissue, which comprises:

a) a cartridge containing a plurality of fasteners;

b) fastener receiving means positioned opposite said cartridge for receiving said fasteners;

c) means for approximating said cartridge toward said fastener receiving means to a fastener firing position to grip body tissue therebetween; and d) means operatively associated with said cartridge for preventing approximation of said cartridge toward said fastener firing position only when said cartridge is spent and while said spent cartridge is loaded in said apparatus.

2. The apparatus of claim 1 wherein the fasteners comprise staples with bendable legs and said fastener receiving means comprises an anvil having depressions for crimping the legs of said staples.

3. The apparatus of claim 1 wherein said fasteners are two-part fasteners comprising a fastener portion and a retainer portion, and said fastener receiving means comprises an assembly for releasably holding the retainer portions.

4. The apparatus of claim 1 further comprising means for substantially simultaneously firing said fasteners.

5. The apparatus of claim 1 further comprising means for detaching said cartridge for removal and replacement thereof.

6. An apparatus for applying a plurality of surgical fasteners to body tissue, which comprises:

a) support means for supporting a cartridge containing a plurality of fasteners;

b) fastener receiving means positioned opposite said cartridge for receiving said fasteners;

c) means for approximating said cartridge toward said fastener receiving means to grip body tissue therebetween; and d) means associated with said cartridge and said fastener receiving means for preventing approximation of said cartridge toward said fastener receiving means only after said fasteners are fired and said cartridge is withdrawn from said fastener receiving means to thereby prevent subsequent approximation of said cartridge from which said fasteners have been fired toward said fastener receiving means while said cartridge is loaded in said apparatus.

7. An apparatus for applying a plurality of surgical fasteners to body tissue, which comprises:

a) support means for supporting a cartridge;
b) a cartridge supported by said support means and containing a plurality of surgical fasteners;
c) fastener receiving means positioned opposite said cartridge for receiving said fasteners;
d) means for approximating said cartridge toward said fastener receiving means to grip body tissue therebetween;
e) a hook mounted for relative movement with respect to said cartridge from a first position when said fasteners are positioned in said cartridge, to a second position in response to firing said fasteners from said cartridge, and to a third position when said cartridge is withdrawn from said fastener receiving means; and
f) means positioned on said support means for interfering with said hook when said hook is in the third position so as to prevent approximation of said cartridge toward said fastener receiving means only when said cartridge is devoid of fasteners and loaded in said support means.

8. A surgical apparatus for applying a plurality of surgical fasteners to body tissue, which includes an anvil and a cartridge for holding the fasteners, said apparatus comprising:

means for approximating said cartridge toward said anvil to grip body tissue therebetween;

means for firing fasteners from said cartridge;

a support for retaining said cartridge in a first position to receive said means for firing fasteners; and a locking mechanism mounted for interaction with said cartridge and moved to a locking position upon withdrawal of said cartridge from the body tissue after firing the fasteners, said locking mechanism in said locking position preventing subsequent approximation of said cartridge toward said anvil with said cartridge in said first position.

9. The apparatus of claim 8, further comprising approximation blocking means for blocking approximation of said cartridge toward said anvil, said locking mechanism being engageable with said approximation blocking means to prevent approximation of the cartridge toward said anvil after said fasteners have been fired from said cartridge.

10. The apparatus of claim 9 further comprising means for substantially simultaneously firing said fasteners.

11. The apparatus of claim 9 further comprising means for removably attaching said cartridge for permitting replacement with another removable cartridge.

12. The apparatus of claim 9, wherein said locking mechanism is at least partially located inside of said cartridge.

13. The apparatus of claim 9, wherein said locking mechanism moves from an initial position within said cartridge to a final position wherein at least a portion of said locking mechanism extends beyond the periphery of said cartridge so as to become engageable with said approximation blocking means.

14. The apparatus of claim 9, wherein said locking mechanism comprises a leaf spring.

15. The apparatus of claim 14, wherein said leaf spring is generally U-shaped and comprises a first arm portion, a second arm portion, a rounded proximal end portion connecting said first and second arm portions, and a detent portion connected to the distal end of the second arm portion and projecting therefrom.

16. The apparatus of claim 15, wherein the approximation blocking means comprises means to engage said detent portion of the leaf spring.

17. The apparatus of claim 16, wherein said means to engage said detent portion comprises a slot.

18. The apparatus of claim 17, wherein said leaf spring is located within a chamber in the cartridge and movable in response to firing of the fasteners from a first position wherein said detent portion is not engageable with said slot to an intermediate position wherein said detent portion is located outside said chamber, and wherein said detent portion is resiliently movable into engagement with said slot in response to proximal movement of the cartridge.

19. The apparatus of claim 9, wherein said fasteners comprise metal staples.

20. The apparatus of claim 9, wherein said fasteners comprise two-part fasteners fabricated from bioabsorbable polymer.

21. The apparatus of claim 20, wherein said bioabsorbable polymer is selected from the group consisting of polyglycolide, polylactide, and glycolide/lactide copolymer.

22. A cartridge for holding surgical fasteners which is adapted for use in a surgical fastener applying apparatus having closure means to approximate the cartridge to body tissue, and having firing means to eject the fasteners from the cartridge, which comprises:

a) slot means for holding a plurality of surgical fasteners;
b) means responsive to the firing means in the fastener applying apparatus for substantially simultaneously driving said surgical fasteners from said slot means; and
c) a locking means operatively associated with said cartridge, said locking means being actuated by movement of the cartridge after firing fasteners for preventing the apparatus from reclosing while loaded with the cartridge from which said fasteners have been fired.

23. The cartridge of claim 18, wherein the surgical fastener applying apparatus possesses blocking means for engaging said locking means to prevent reclosure of the apparatus, said locking means engaging said blocking means only after the fasteners have been fired.

24. The cartridge of claim 23, wherein said actuation of said locking means comprises movement of said locking mechanism from an initial position within the cartridge to a final position wherein at least a portion of said locking means extends beyond the periphery of the cartridge so as to become engageable with said blocking means.

25. The cartridge of claim 24, wherein said blocking means comprises a slot.

26. The cartridge of claim 24, wherein said locking means comprises a leaf spring.

27. The cartridge of claim 26, wherein said leaf spring is generally U-shaped and integrally comprises a first arm portion, a second arm portion, a rounded proximal end portion connecting said first and second arm portions, and a detent portion connected to the distal end of the second arm portion and projecting therefrom.

28. An apparatus for applying a plurality of surgical fasteners to body tissue comprising:

a) a frame defining a longitudinal axis;
b) a cartridge mounted to said frame and containing a plurality of fasteners, said cartridge mounted for movement along said longitudinal axis of said frame between a proximal open position and a distal firing position;
c) an anvil positioned opposite said cartridge for crimping said fasteners;

d) an actuation mechanism for moving said cartridge between said proximal open position and said distal firing position in close approximation to said anvil to grip body tissue;

e) a locking mechanism mounted for interaction with said cartridge, said locking mechanism preventing movement of said cartridge along said longitudinal axis from said open position to said firing position only after said cartridge has been fired and retracted proximally to said open position, and while said cartridge from which said fasteners have been fired is loaded in said apparatus; and f) a firing mechanism for firing the fasteners.

29. The apparatus of claim 24, wherein said locking mechanism comprises a member disposed in said cartridge and engageable with a slotted portion of the apparatus.

30. The apparatus of claim 29, wherein said anvil is disposed in an anvil support arm and said slotted portion is formed in said anvil support arm.

31. The apparatus of claim 28, wherein said locking mechanism is initially actuated by said firing mechanism for firing the fasteners and further actuated by retraction of said cartridge.

32. The apparatus of claim 31, wherein said cartridge is removable.

33. An apparatus for applying a plurality of surgical fasteners to body tissue, which comprises:

a) first and second spaced-apart opposing jaws defining a closable gap for the reception and engagement of body tissue therebetween, said first jaw comprising a cartridge for holding a plurality of surgical fasteners and said second jaw comprising an anvil for closing said surgical fasteners, said gap being closable by approximation of said jaws;

b) an actuation mechanism for approximating said jaws for closing said gap;

c) a firing mechanism for firing said surgical fasteners from said cartridge; and d) a locking mechanism mounted for interaction with said cartridge to prevent relative movement of said jaws with said cartridge loaded in said apparatus and spent of fasteners, wherein actuation of said locking mechanism is responsive to firing of said fasteners.

34. The apparatus of claim 33, wherein said firing mechanism comprises means for simultaneously ejecting the fasteners from said cartridge.

35. The apparatus of claim 33, wherein said locking mechanism comprises a locking clip and a blocking means for preventing relative movement of said jaws, said locking clip being movable in response to the firing of said fasteners from a first position wherein said locking clip is not engageable with said blocking means to a second position wherein said locking clip is engageable with said blocking means.

36. The apparatus of claim 33, wherein said surgical fasteners are fabricated from a bioabsorbable material.

37. The apparatus of claim 33, wherein said first jaw is movable between a first position whereby said gap is open for the reception of body tissue, and an approximated second position wherein said gap is closed.

38. The apparatus of claim 37, wherein said locking mechanism includes a locking clip and a blocking means for preventing relative movement of said jaws, said locking clip being movable in response to firing of said fasteners from an initial position wherein said locking clip is not engaged with said blocking means, to a second position wherein said locking clip is engaged with said blocking means.

39. A staple cartridge assembly adapted for use in a surgical stapler having a cartridge retention portion and an anvil portion, said portions being relatively movable between a closed position in which the cartridge retention and anvil portions are in closely spaced relationship for clamping tissue to be stapled therebetween and an open position with the cartridge retention and anvil portions spaced farther from each other than in the closed position, said cartridge assembly comprising:

a cartridge housing for enclosing staples, a firing assembly for firing staples which is movable between a pre-fired and a fired position, a safety member, means mounting the safety member on said cartridge housing for movement between a free-movement position which affords movement of said cartridge retention portion and said anvil portion between said open and closed positions and a blocking position which prevents said cartridge retention portion and said anvil portion from being moved to said closed position, and means for retaining said safety member in said free-movement position and for affording movement of said safety member toward said blocking position when said firing assembly is moved from said pre-fired to said fired position such that upon movement of the cartridge retention portion and anvil portion to the open position, the safety member prevents the cartridge retention portion and the anvil portion from thereafter being moved to the closed position while the stapler is loaded with the spent cartridge.

40. In a surgical stapler having an anvil surface, a cartridge housing containing staples, the cartridge housing and the anvil surface being relatively movable between a closed position in which the cartridge housing and the anvil surface are in closely spaced relationship for clamping tissue to be stapled therebetween and an open position with the cartridge housing and anvil surface spaced farther from each other than in the closed position, and a firing assembly for firing staples which is movable between a prefired position and a fired position, the improvement comprising:

a safety member interacting with the cartridge assembly and mounted for movement between a free movement position affording relative movement of the cartridge housing and the anvil surface between the open and closed positions and a blocking position preventing relative movement of the cartridge housing and the anvil surface from the open position to the closed position, and a mechanism for retaining the safety member in the free movement position and for affording movement of the safety member to the blocking position upon relative movement of the cartridge housing and the anvil surface toward the open position after the staples have been fired, such that the safety member prevents the cartridge housing and anvil surface from thereafter being relatively moved to the closed position while the stapler is loaded with the cartridge housing from which the staples have been fired.

41. A surgical stapler comprising:

an anvil frame elongate in a longitudinal direction and including anvil surfaces in a plane generally perpendicular to the longitudinal direction, a cartridge assembly movable relative to the anvil frame between an open position with the cartridge assembly spaced from the anvil surfaces and a closed position with the cartridge assembly and the anvil surfaces in closely spaced relationship, the cartridge assembly including a cartridge housing containing a plurality of staples disposed in at least one row positioned in opposition to the anvil surfaces, and a pusher mechanism movable in a longitudinal direction for pressing the staples within the cartridge housing against the anvil surfaces to engage and close the staples in tissue between the cartridge housing and the anvil surfaces, the pusher mechanism being movable relative to the cartridge housing between pre-fired and fired positions; and an engaging member interacting with the cartridge assembly and mounted for engagement with the cartridge assembly for preventing the cartridge assembly from moving from the open to the closed position when the stapler is loaded with a cartridge housing having a pusher mechanism disposed in a fired position.

42. Apparatus as recited in claim 41, wherein an elongated drive shaft engages the pusher mechanism to effect the longitudinal movement thereof.

43. Apparatus for applying a plurality of surgical fasteners to body tissue, which comprises:

a) a cartridge containing a plurality of surgical fasteners and means for holding said cartridge;

b) fastener closing means for closing fasteners after they have been at least partially expelled from said cartridge;

c) means for moving said cartridge between a proximal first position and a distal second position wherein said cartridge is in close approximation to fastener closing means;

d) means for substantially simultaneously ejecting said fasteners from said cartridge for closure thereof by said fastener closing means;

e) approximation blocking means for preventing movement of said cartridge to said distal second position; and f) a locking member interacting with said cartridge and mounted for movement in response to ejection of said fasteners said locking member moving to a locking position upon movement of said cartridge from said second position to engage said approximation blocking means to prevent movement of said cartridge from said first position to said second position.

44. The apparatus of claim 43, wherein said locking member is joined to the cartridge and is at least partially located inside the cartridge.

45. The apparatus of claim 44, wherein the cartridge is removable and replaceable.

46. The apparatus of claim 43, wherein said approximation blocking means comprises a surface for blocking distal movement of the locking member.

47. The apparatus of claim 43, wherein said locking member is slidably mounted within the cartridge and is movable from a first position to a second position wherein it is engageable with said approximation blocking means.

48. The apparatus of claim 43, wherein said fasteners comprise metal staples.

49. The apparatus of claim 43, wherein said fasteners comprise two-part fasteners fabricated from bioabsorbable polymer, said two-part fasteners comprising a fastener portion and a retainer portion.

50. The apparatus of claim 49, wherein said bioabsorbable polymer is selected from the group consisting of polyglycolide, polylactide, and glycolide/lactide copolymer.

51. An apparatus for applying a plurality of surgical fasteners to body tissue comprising:

a) an anvil;

b) a cartridge containing a plurality of surgical fasteners, the cartridge and anvil being relatively movable between a first spaced apart position and a second position in close approximation with one another;

c) a pusher mechanism movable through the cartridge for ejecting the surgical fasteners from the cartridge to be driven against the anvil; and d) a locking member interacting with the cartridge and mounted for movement in response to movement of said pusher mechanism, said locking member moving to a blocking position, the locking member in the blocking position preventing relative movement of the anvil and the cartridge.

52. An apparatus as recited in claim 51, wherein the cartridge is configured as a removable and replaceable unit.

53. An apparatus as recited in claim 51, wherein the anvil defines a fastener forming surface including at least one row of depressions arranged perpendicular to the direction of movement of the pusher mechanism.

54. An apparatus as recited in claim 51, wherein the surgical fasteners comprise metal staples.

* * * * *